United States Patent
Ohsaka (10) Patent No.: US 12,421,487 B2
(45) Date of Patent: *Sep. 23, 2025

(54) CELL SCREENING DEVICE AND CELL SCREENING KIT

(71) Applicant: Tokyo Ohka Kogyo Co., Ltd., Kawasaki (JP)

(72) Inventor: Takashi Ohsaka, Kawasaki (JP)

(73) Assignee: TOKYO OHKA KOGYO CO., LTD., Kawasaki (JP)

( * ) Notice: Subject to any disclaimer, the term of this patent is extended or adjusted under 35 U.S.C. 154(b) by 707 days.

This patent is subject to a terminal disclaimer.

(21) Appl. No.: 17/753,497

(22) PCT Filed: Sep. 28, 2020

(86) PCT No.: PCT/JP2020/036530
§ 371 (c)(1),
(2) Date: Mar. 4, 2022

(87) PCT Pub. No.: WO2021/065765
PCT Pub. Date: Apr. 8, 2021

(65) Prior Publication Data
US 2022/0340859 A1    Oct. 27, 2022

(30) Foreign Application Priority Data

Sep. 30, 2019   (JP) ................................ 2019-178992

(51) Int. Cl.
*C12M 1/34* (2006.01)
*C12M 1/00* (2006.01)
(Continued)

(52) U.S. Cl.
CPC ............ *C12M 41/32* (2013.01); *C12M 23/12* (2013.01); *C12M 23/44* (2013.01); *C12M 23/48* (2013.01);
(Continued)

(58) Field of Classification Search
None
See application file for complete search history.

(56) References Cited

U.S. PATENT DOCUMENTS

| 5,961,799 A | 10/1999 | Matsumoto et al. |
| 2002/0182645 A1 | 12/2002 | Milteny |

(Continued)

FOREIGN PATENT DOCUMENTS

| CN | 103415774 A | 11/2013 |
| CN | 107407691 A | 11/2017 |

(Continued)

OTHER PUBLICATIONS

Document entitled WO2018105608A1 Particle Capture Device, machine translation of WO 2018/105608 A1 provided by Espacenet, original document published 2018. (Year: 2018).*

(Continued)

*Primary Examiner* — Michael A Marcheschi
*Assistant Examiner* — Ashley Lopezlira
(74) *Attorney, Agent, or Firm* — KNOBBE, MARTENS, OLSON & BEAR, LLP (57) ABSTRACT

A cell screening device including a bottom plate, a cell placement membrane, a pair of fluid injection parts, and a flow channel, the flow channel being formed between the bottom plate and the cell placement membrane and extending in such a manner that the flow channel end parts respectively reach the fluid injection parts. In the cell placement membrane, a plurality of wells, each having a size capable of housing a single cell, and through holes are formed. In the back side of each lid, i.e., the ceiling face of the flow channel end part, a debubbling surface, which rises in an inclined or step-like manner as getting closer to a fluid injection hole, is formed.

13 Claims, 10 Drawing Sheets

(51) Int. Cl.
*C12M 1/12* (2006.01)
*C12M 1/32* (2006.01)
*C12M 3/00* (2006.01)
*G01N 33/569* (2006.01)

(52) U.S. Cl.
CPC ............ *C12M 25/02* (2013.01); *C12M 29/20* (2013.01); *C12M 47/04* (2013.01); *G01N 33/56972* (2013.01)

(56) References Cited

U.S. PATENT DOCUMENTS

| | | |
|---|---|---|
| 2013/0345088 A1 | 12/2013 | Noji et al. |
| 2016/0045884 A1 | 2/2016 | Husain |
| 2016/0289669 A1 | 10/2016 | Fan et al. |
| 2017/0067006 A1* | 3/2017 | Obi .................. C12M 23/12 |
| 2017/0189907 A1 | 7/2017 | Tibbe |
| 2018/0282677 A1 | 10/2018 | Ohsaka et al. |
| 2019/0366340 A1 | 12/2019 | Govyadinov |
| 2020/0123484 A1* | 4/2020 | Tseng .................. C12M 23/16 |
| 2020/0362294 A1 | 11/2020 | Suzuki et al. |
| 2022/0113233 A1 | 4/2022 | Kato |
| 2022/0297127 A1 | 9/2022 | Ohsaka |
| 2022/0340859 A1 | 10/2022 | Ohsaka |

FOREIGN PATENT DOCUMENTS

| | | | |
|---|---|---|---|
| CN | 110036104 A | 7/2019 | |
| JP | 11-509420 A | 8/1999 | |
| JP | 2017-518752 A | 7/2017 | |
| JP | 2018-121568 A | 8/2018 | |
| JP | 2019-146548 A | 9/2019 | |
| WO | WO 97/04074 A1 | 2/1997 | |
| WO | WO 2015/087370 A1 | 6/2015 | |
| WO | WO 2015/191684 A1 | 12/2015 | |
| WO | WO 2015/198866 A1 | 12/2015 | |
| WO | WO 2017/057234 A1 | 4/2017 | |
| WO | WO-2018105608 A1 * | 6/2018 | ........ B01L 3/502761 |
| WO | WO 2019/069900 A1 | 4/2019 | |
| WO | WO 2019/167951 A1 | 9/2019 | |
| WO | WO 2021/065765 A1 | 4/2021 | |
| WO | WO 2021/065771 | 4/2021 | |

OTHER PUBLICATIONS

Office Action received in U.S. Appl. No. 17/693,500, dated Nov. 29, 2024.

* cited by examiner

CELL SCREENING DEVICE AND CELL SCREENING KIT

TECHNICAL FIELD

The present invention relates to a cell screening device and a cell screening kit for screening cells. Priority is claimed on Japanese Patent Application No. 2019-178992, filed Sep. 30, 2019, the content of which is incorporated herein by reference.

BACKGROUND ART

In recent years, particularly in the field of drug discovery, the target of cell analysis has been subdivided from the cell group level to the single cell level, and a method has been used in which a cell screening device is used to catch cells one by one in minute wells and then a large number of cells are subjected to a screening test at once to select cells having the desired characteristics. As the method of screening cells, for example, a method has been adopted in which cells caught in a large number of wells are brought into contact with a solution obtained by dispersing a reagent such as a capture that binds to a specific antibody, cells that have secreted a secretion product bound to the catcher are identified, and then the identified cells are recovered from the wells.

Patent Document 1 discloses a cell screening device that was previously proposed by the present applicants and the like. This cell screening device has a first substrate and a second substrate that are disposed so as to be horizontally stacked, a large number of wells in which cells can be accommodated one by one are formed on the surface of the first substrate, and communication holes that reach the back surface of the first substrate from the bottom surfaces of the respective wells are formed individually. These communication holes are so small that cells cannot pass therethrough. On the second substrate, an accumulation part that receives the secretion product flowing out of the well through the communication hole is formed, and the secretion product and the reagent are reacted at the accumulation part to identify the target cell.

CITATION LIST

Patent Document

Patent Document 1

PCT International Publication No. WO2017/057234A1 Pamphlet

SUMMARY OF INVENTION

Technical Problem

In a cell screening device as disclosed in Patent Document 1, it is necessary to provide a reagent introduction part in order to supply a liquid such as a reagent or a dispersion liquid to the accumulation part. For example, in a case where a reagent introduction part is provided at the end part of the device, small air bubbles may enter the reagent introduction channel in a case where a reagent or a dispersion liquid is injected in or taken out through the reagent introduction part using an instrument such as a pipette, a micropipette, a dispenser, or the like, or in a case where the device is inclined and thus the liquid level inside the reagent introduction part drops. In a case where such air bubbles enter the reagent introduction channel, there is the risk that, for example, the air bubbles move to the flow channel, block the back side of the cell placement membrane, and obstruct the fluid flow between the well and the flow channel, thereby affecting screening.

Solution to Problem

A cell screening device according to an aspect [1] of the present invention includes a bottom plate part; a cell placement part that is provided on the bottom plate part and is configured to constitute a cell placement surface; a fluid injection part that is provided on the bottom plate part, separately from the cell placement part; a plurality of wells that are formed on the cell placement surface of the cell placement part and have a size in which cells to be screened are individually accommodatable; a flow channel that is provided between the bottom plate part and the cell placement part, where a flow channel end part extends to the fluid injection part; a through-hole that leads to the flow channel from an inner bottom surface of the well and has an inner diameter through which the cells to be screened are not passable; a lid part that is provided in the fluid injection part and blocks the flow channel end part; and a fluid injection hole that is provided in the lid part and leads to the flow channel, where in the lid part, a bubble discharge surface is formed on at least a part of a ceiling surface of the flow channel end part, the bubble discharge surface rising in an inclined surface shape or a stepped shape as the bubble discharge surface approaches the fluid injection hole.

According to such a cell screening device, in a case where a reagent or a dispersion liquid is injected in or taken out through the fluid injection hole using an instrument such as a pipette, a micropipette, a dispenser, or the like, or in a case where the device is inclined and thus the liquid level inside the flow channel end part drops, since a bubble discharge surface is formed on at least a part of the back side of the lid part, that is, a ceiling surface of the flow channel end part, the bubble discharge surface rising in an inclined surface shape or a stepped shape as it approaches the fluid injection hole, air bubbles move toward the fluid outlet along the bubble discharge surface and then become discharged from the fluid outlet even in a case where air bubbles enter the flow channel end part. Accordingly, it is difficult for air bubbles to enter the flow channel, and thus it is possible to reduce the risk that, for example, screening is affected.

In the cell screening device of an aspect [2], according to the aspect [1], the bubble discharge surface is formed over an entire surface of the ceiling surface of the flow channel end part in the lid part. In this case, air bubbles move toward the fluid outlet along the bubble discharge surface and then become discharged from the fluid outlet even in a case where air bubbles are present in any position inside the flow channel end part.

In the cell screening device of an aspect [3], according to the aspect [1], the bubble discharge surface is partially formed around the fluid injection hole of the ceiling surface of the flow channel end part in the lid part. In this case, the air bubbles that have entered from the fluid injection hole move toward the fluid outlet along the air bubble discharge surface formed around the fluid injection hole and then become discharged from the fluid outlet. In addition, there is an advantage in that the degree of freedom in the design of the cell screening device is increased by partially forming the bubble discharge surface.

In the cell screening device of an aspect [4], according to any one of the aspects [1] to [3], the bubble discharge surface is an inclined surface having a linear cross-sectional or curved cross-sectional shape, which is inclined by 5° to 45° with respect to a lower surface of the bottom plate part. In this case, since the inclination angle is set as described above, air bubbles move toward the fluid outlet without delay along the inclined surface of the air bubble discharge surface, and the reliability that the air bubbles are discharged from the fluid outlet is increased. In addition, the degree of protrusion of the lid part at the fluid outlet can be suppressed to be relatively small while air bubbles are effectively discharged.

In the cell screening device of an aspect [5], according to any one of the aspects [1] to [4], the bottom plate part has a rectangular shape having a long side and a short side, the fluid injection part, the lid part, the fluid injection hole, and the bubble discharge surface are each formed on both sides of the bottom plate part in a longitudinal direction, and the cell placement part is disposed between the two lid parts. In this case, a wide range of usage methods, for example, causing the fluid to flow from one of the two fluid injection holes into the flow channel and causing the excess fluid to be discharged from the other fluid injection hole is possible, and furthermore, in this process, since air bubbles move toward the fluid outlet along the bubble discharge surface and become discharged from the fluid outlet, it is possible to suppress problems due to the air bubbles. However, the present invention is not limited to the constitution in which two fluid injection holes are provided, and as necessary, only one fluid injection hole may be provided, or three or more fluid injection holes can also be provided.

In the cell screening device of an aspect [6], according to the aspects [1] to [5], the cell placement part is a membrane body, a plurality of the wells are formed on an upper surface of the membrane body in a lattice form, and the through-hole that leads to the inner bottom surface of each of the wells is formed on a lower surface of the membrane body, a frame body that supports a periphery of the membrane body and surrounds the cell placement surface is provided, and an engaging part for attachably and detachably fixing the frame body is provided in the bottom plate part. In this case, in a case where a frame body is engaged with an engaging part of the bottom plate part, the membrane body having the wells is positioned at the correct position on the bottom plate part, and the frame body can be removed from the bottom plate part after screening.

In the cell screening device of an aspect [7], according to any one of the aspects [1] to [6], a peripheral wall portion that stands up from a circumference of the lid part is formed, and the lid part and the peripheral wall portion are formed as an outer frame body that is attachable to and detachable from the bottom plate part. In this case, the lid part and the peripheral wall portion can be accurately positioned simply by forming the bottom plate part and the outer frame body as separate ones and attaching the outer frame body to the bottom plate part, and thus assembly is easy. In addition, after use, disassembly can be easily carried out by removing the outer frame body from the bottom plate part, which facilitates maintenance.

In the cell screening device of an aspect [8], according to the aspect [6], a standing peripheral wall portion is formed in a circumference of the lid part, the lid part and the peripheral wall portion are formed as an outer frame body that is attachable to and detachable from the bottom plate part, and the frame body that supports the membrane body is attachably and detachably fixed to the outer frame body.

In this case, the membrane body, the lid part, and the peripheral wall portion can be accurately positioned simply by forming each of the bottom plate part, the outer frame body, and the frame body as separate ones and attaching the frame body and the outer frame body to the bottom plate part, and thus the ease of assembly can be improved. In addition, after use, it is also possible to remove the frame body and the outer frame body from the bottom plate part, which facilitates maintenance.

In the cell screening device of an aspect [9], according to the aspects [1] to [8], the bottom plate part has a rectangular shape having a long side and a short side, the fluid injection part, the lid part, the fluid injection hole, and the bubble discharge surface are each formed on both sides of the bottom plate part in a longitudinal direction, the cell placement part is disposed between the two lid parts, and the lid part, a peripheral wall portion that stands up from a circumference of each lid part, and a peripheral wall portion that surrounds a periphery of the cell placement part are formed as an outer frame body that is attachable to and detachable from the bottom plate part. In this case, the cell placement part, the lid part, the peripheral wall portion, and two fluid injection holes can be accurately positioned simply by forming the bottom plate part and the outer frame body as separate ones, and attaching the outer frame body to the bottom plate part, and thus the ease of assembly can be improved. In addition, after use, disassembly can be easily carried out by removing the outer frame body from the bottom plate part, which facilitates maintenance.

In the cell screening device of an aspect [10], according to any one of the aspects [1] to [9], a tubular port that stands up from the fluid injection hole is formed in the lid part. In this case, since the fluid injection port has a tubular shape, the pointed tip of the pipette or dispenser can be applied to the tip of the fluid injection port, whereby a fluid can be easily injected in or taken out.

The cell screening kit of an aspect [11] includes the cell screening device according to any one of the aspects of [1] to [10], and a detection particle that is a carrier particle on which a substance having a binding property to a secretion product of cells to be screened is immobilized. According to this cell screening kit, in a state where cells are incorporated into individual wells, detection particles and secretion product of cells are reacted in the wells, and screening can be carried out by luminescence from the detection particles. Moreover, in a case where a reagent or a dispersion liquid is injected in or taken out through the fluid injection hole using an instrument such as a pipette, a micropipette, a dispenser, or the like, or in a case where the device is inclined and thus the liquid level inside the flow channel end part drops, since a bubble discharge surface is formed on at least a part of the back side of the lid part, that is, a ceiling surface of the flow channel end part, the bubble discharge surface rising in an inclined surface shape or a stepped shape as it approaches the fluid injection hole, air bubbles move toward the fluid outlet along the bubble discharge surface and then become discharged from the fluid outlet even in a case where air bubbles enter the flow channel end part. Accordingly, it is difficult for air bubbles to enter the flow channel, and thus the risk that, for example, screening is affected is low.

Advantageous Effects of Invention

As described above, according to the cell screening device or the cell screening kit of the present invention, in a case where a reagent or a dispersion liquid is injected in or taken out through the fluid injection hole using an instrument, or in a case where the device is inclined and thus the liquid level inside the flow channel end part drops, since a bubble discharge surface is formed on at least a part of the back side of the lid part, that is, a ceiling surface of the flow channel end part, where the bubble discharge surface rises as it approaches the fluid injection hole, air bubbles are discharged from the fluid outlet along the bubble discharge surface even in a case where air bubbles enter the flow channel end part. Accordingly, it is difficult for air bubbles to enter the flow channel, and thus an effect of reducing the risk that, for example, screening is affected is exhibited.

DESCRIPTION OF EMBODIMENTS

Figure 5:
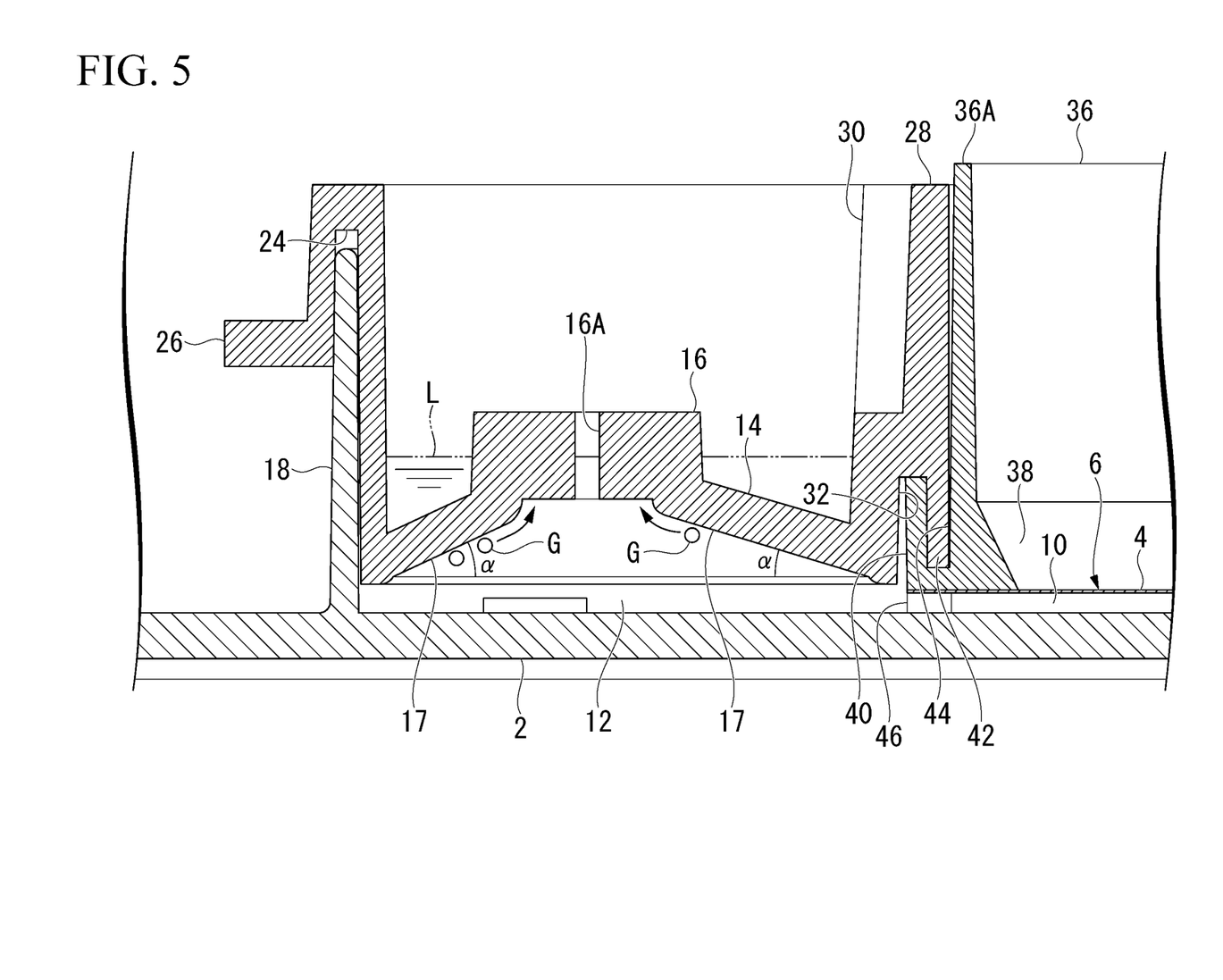
FIG. 5 is a real cross-sectional view of an end part of the cell screening device according to the same embodiment.
Figure 6:
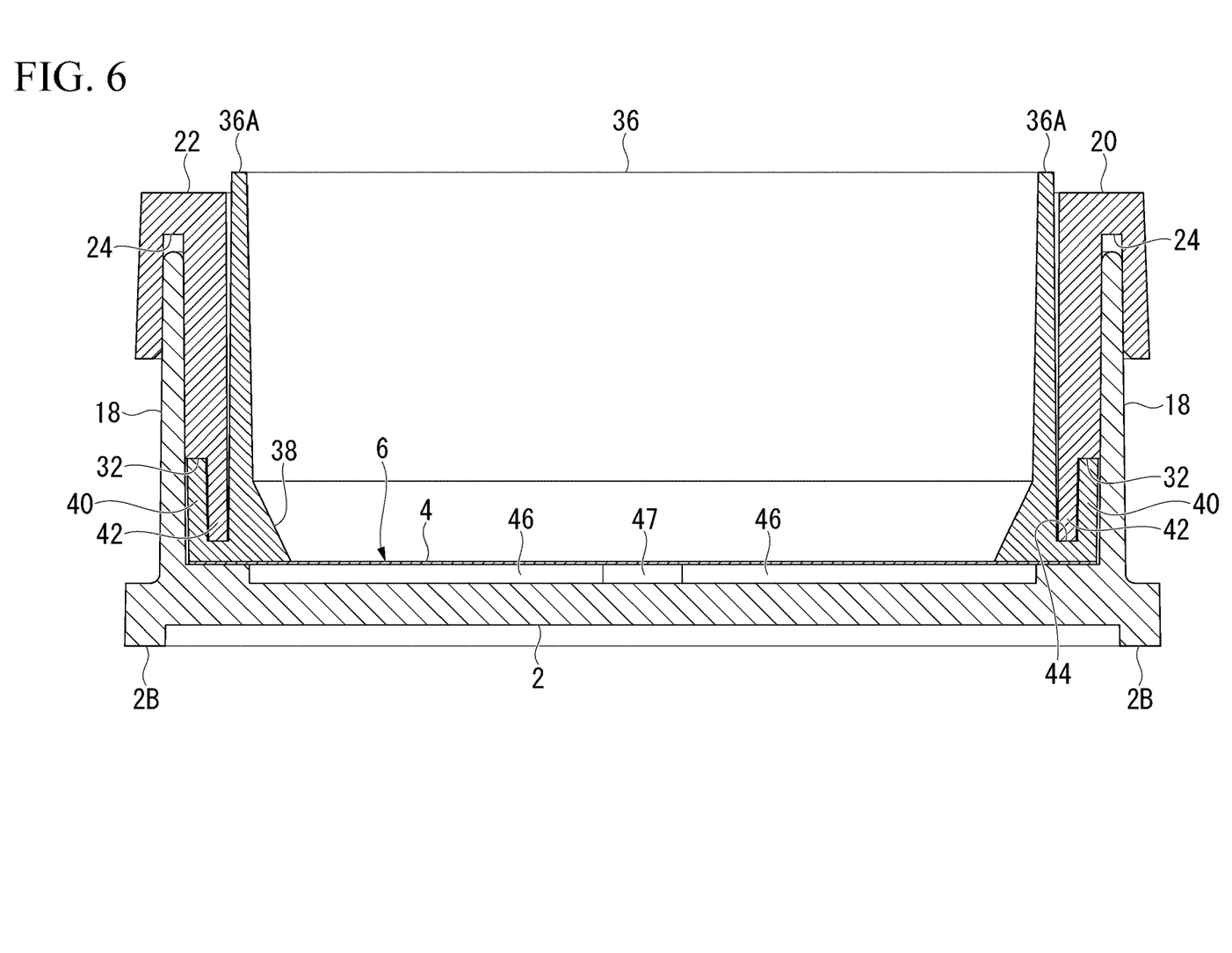
FIG. 6 is a side sectional view of the cell screening device according to the same embodiment.
Figure 7:
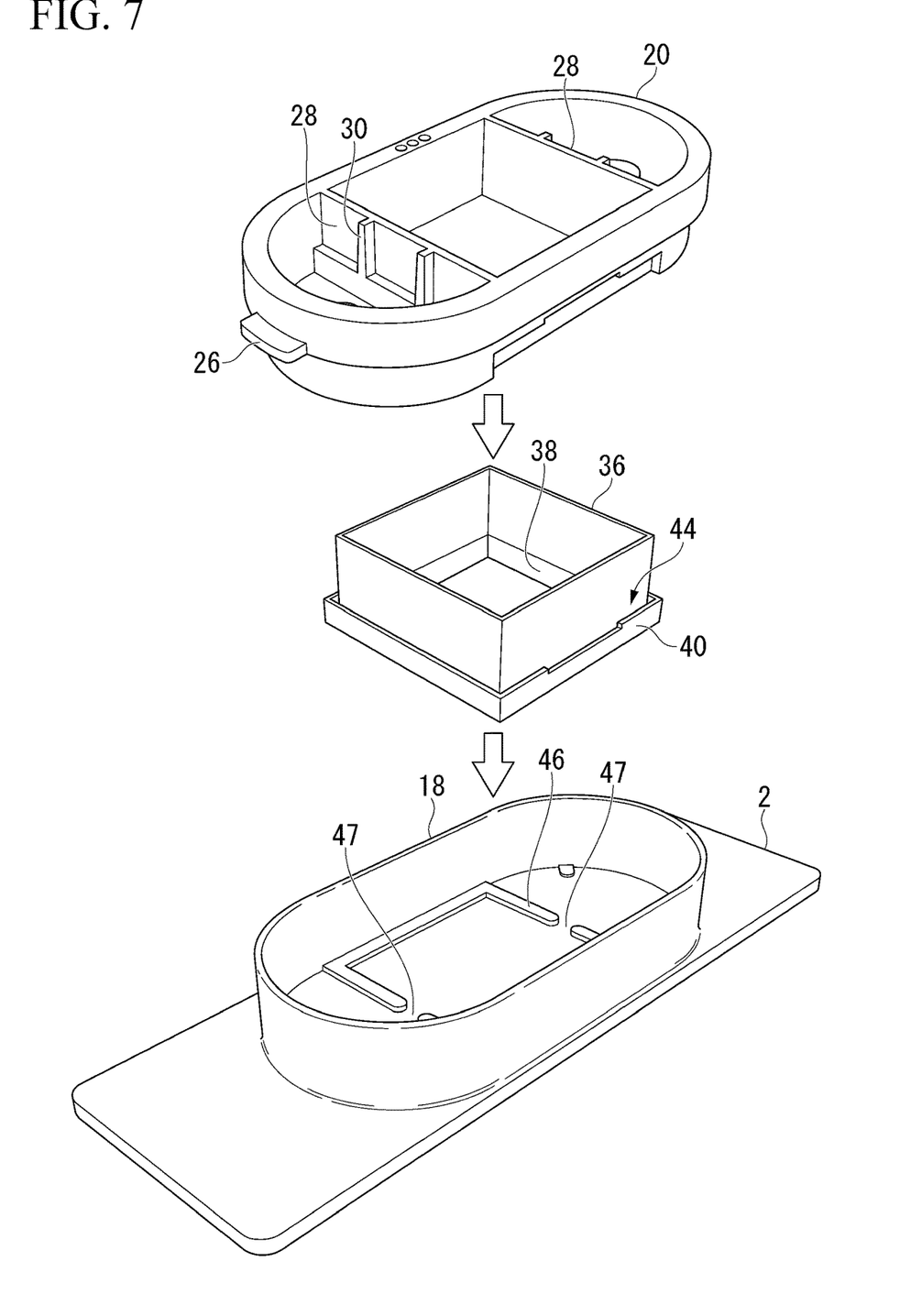
FIG. 7 is a perspective view showing an assembly method of the cell screening device according to the same embodiment.
Figure 8:
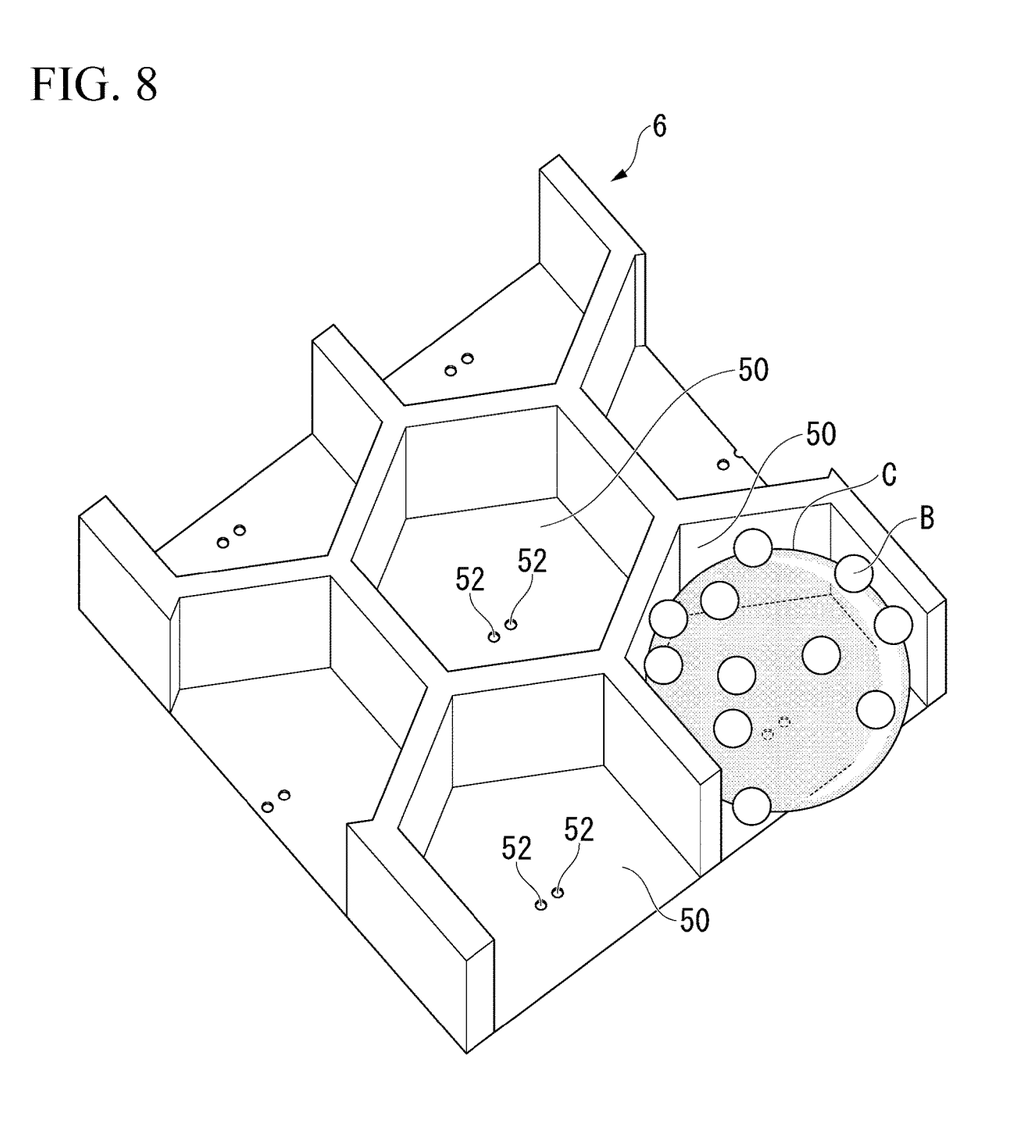
FIG. 8 is an enlarged perspective view showing a cell placement membrane (a cell placement part) and a well of the cell screening device according to the same embodiment.

FIG. 1 to FIG. 6 all show a completed state of a cell screening device 1 according to the embodiment of the present invention, and FIG. 7 shows a method of assembling the cell screening device 1. A cell screening device 1 of this embodiment has a bottom plate part 2; a cell placement membrane (a cell placement part) 6 that is provided on the bottom plate part 2 and is configured to constitute a cell placement surface 4; a pair of fluid injection parts 8 that are provided on the bottom plate part 2, separately from the cell placement membrane 6; and a flow channel 10 that is provided between the bottom plate part 2 and the cell placement membrane 6, a flow channel end part 12 of which extends to the fluid injection part 8. On the cell placement surface 4 of the cell placement membrane 6, for example, as shown in FIG. 8, a plurality of wells 50 having a size capable of individually accommodating cells C to be screened, and a through-hole 52 that leads to the flow channel 10 from the inner bottom surface of the wells 50 are formed, and the through-hole 52 has an inner diameter through which the cells C to be screened cannot pass. Further, a bubble discharge surface 17 that rises in an inclined surface shape as it approaches a fluid injection hole 16A is formed on the back side of each lid part 14, that is, on the ceiling surface of the flow channel end part 12.

Hereinafter, the structure of the cell screening device 1 will be described in detail. The bottom plate part 2 of this example has an elongated rectangular plate shape having a constant thickness, and the four corners are chamfered. A ridge 2B having a constant height is formed on the bottom plate part 2 over the entire circumference along the outer circumference of the bottom surface. The shape of the bottom plate part 2 is not limited to the one shown in the drawing, and it may be any shape such as a disk shape, an elliptical shape, or a square shape. In a case where a horizontal flow channel 10 can be formed, the thickness of the bottom plate part 2 may not be constant. Generally, it is desirable that, in terms of molding accuracy and cost, the bottom plate part 2 be made of various plastics that are harmless to the target cells; however, as necessary, it may be made of any material such as ceramic, glass, or metal. The surface of the bottom plate part 2 may be subjected to some kind of coating for alleviating the influence on cells.

Figure 3:
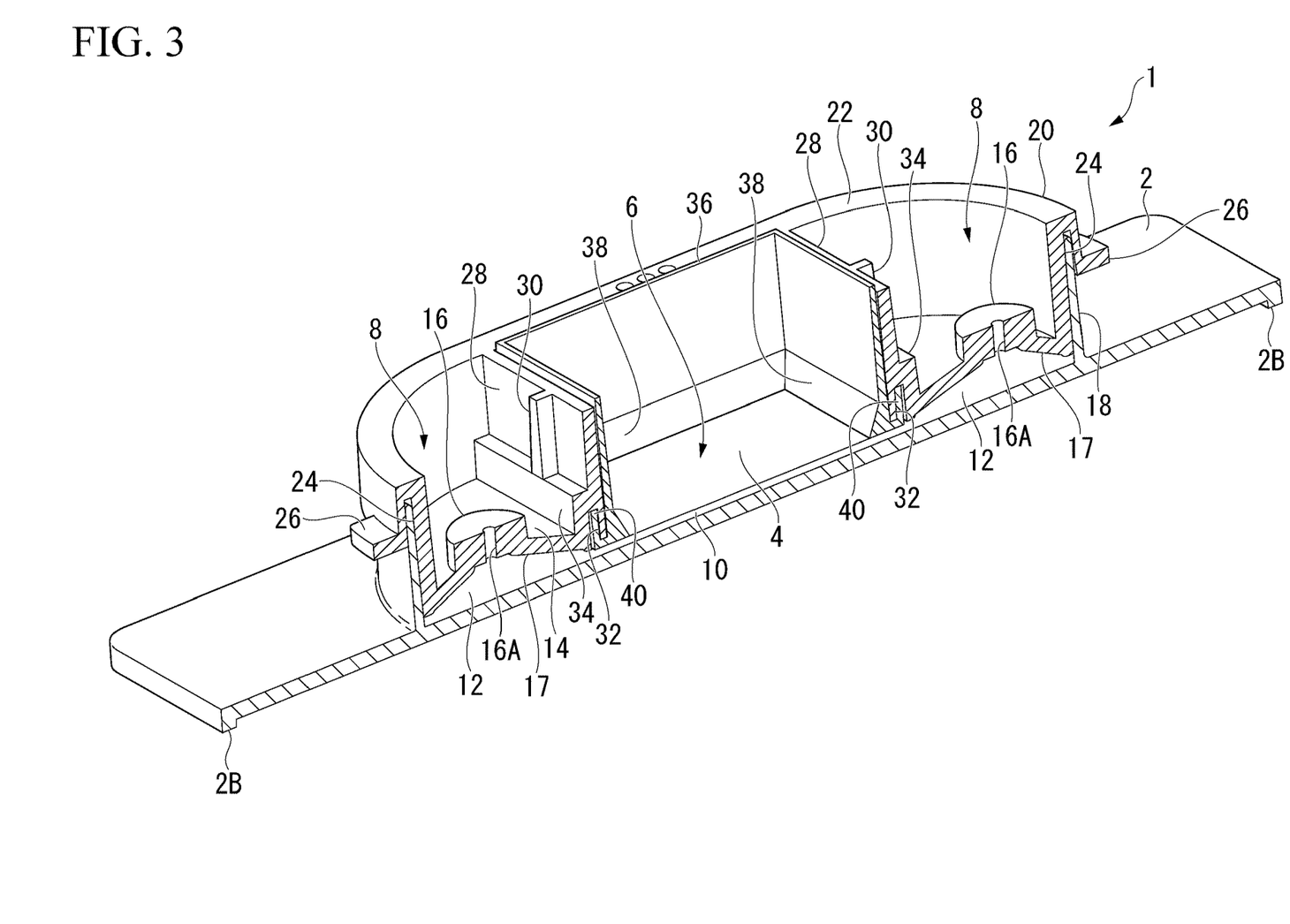
FIG. 3 is a perspective view showing a real cross section of the cell screening device according to the same embodiment.

As shown in FIG. 3, on the upper surface of the bottom plate part 2, an engagement wall 18 having a rectangular shape, both ends of which have a semicircular shape in plan view, is integrally formed to surround the central part in a state of vertically standing up from the bottom plate part 2. The shape of the engagement wall 18 is not limited to the shape shown in the drawing, and it may be a simple rectangular shape, a circular shape, an elliptical shape, or the like. The height of the engagement wall 18 in this example is set to be equal over the entire circumference. An outer frame body 20 is attachably and detachably attached to the engagement wall 18 to cover the engagement wall 18 from above over the entire circumference.

The outer frame body 20 has a rectangular peripheral wall portion 22 having a rectangular shape, both ends of which have a semicircular shape in plan view, and a pair of partitioned parts 28 provided parallel to each other on the inner circumference side of the peripheral wall portion 22, and the whole is integrally formed. The material of the outer frame body 20 is not limited, and it is generally desirable that, in terms of molding accuracy and cost, the outer frame body 20 be made of various plastics that are harmless to the target cells; however, as necessary, it may be made of any material such as ceramic, glass, or metal. A rectangular parallelepiped space is opened between the partitioned part 28 and the partitioned part 28, and the cell placement membrane 6 is disposed in this space.

The upper end of the peripheral wall portion 22 of the outer frame body 20 has a cross-sectional shape in which it is folded outward over the entire circumference, and inside this folded portion, a narrow engagement groove 24 that opens downward is formed at a constant depth over the entire circumference. The upper end part of the engagement wall 18 is inserted into the engagement groove 24 over the entire circumference, and elastically tightened at the folded portion of the peripheral wall portion 22, whereby the outer frame body 20 is attachably and detachably fixed to the engagement wall 18. Protrusions 26 that protrude horizontally are formed at both tips of the outer frame body 20 in the longitudinal direction, and in a case where these protrusions 26 are lifted with a fingertip, the engagement wall 18 comes out from the engagement groove 24, whereby the bottom plate part 2 can be separated from the outer frame body 20.

Each semicircular region surrounded by the peripheral wall portion 22 of the outer frame body 20 and each partitioned part 28 serves as the fluid injection part 8. In these fluid injection parts 8, the lid part 14 having a three-dimensional shape in which a semicircular shape is formed in plan view and the center rises upward is formed so that the lower end of the peripheral wall portion 22 and the lower end of each partitioned part 28 are connected.

A flow channel end part 12 that is both ends of the flow channel 10 is formed between the lid part 14 and the bottom plate part 2, and the lid part 14 has a structure that airtightly blocks the flow channel end part 12. Since the lid part 14 is formed in this manner, the flow channel end part 12 that is both ends of the flow channel 10 is sealed, which prevents a fluid excessively flowing sideways through the flow channel 10 and the flow channel end part 12 even in a case where the cell screening device 1 is inclined or shaken.

In this embodiment, a fluid injection hole 16A having a circular shape is formed in one place at a substantially center of each lid part 14, and a fluid injection port 16 having a circular shape is formed upright from each lid part 14, in a manner matching with the fluid injection hole 16A. The surface of the lid part 14 around the fluid injection port 16 serves as a fluid storage part, and as shown in FIG. 5, a fluid L overflowing from the fluid injection port 16 is accumulated. As the fluid storage part, a recessed part may be proactively formed around the fluid injection port 16 on the upper surface of the lid part 14.

The bubble discharge surface 17 that rises in an inclined surface shape as it approaches a fluid injection hole 16A is formed on the back side of each lid part 14, that is, on the ceiling surface of the flow channel end part 12, and the bubble discharge surface 17 has a truncated cone shape with a fluid injection hole 16A as the apex. As a result, in a case where the flow channel end part 12 is filled with a liquid such as a dispersion liquid and contains air bubbles G, it is configured such that the air bubbles G move smoothly along the bubble discharge surface 17 toward the fluid injection hole 16A due to buoyancy and become discharged from the fluid injection hole 16A.

The angle α formed by the bubble discharge surface 17 and the horizontal plane is not constant in the periphery of the fluid injection hole 16A since the distance between the fluid injection hole 16A and the circumference of the lid part 14 is not constant; however, it is preferably 5° to 45° and more preferably 10° to 30° from the viewpoint of the discharge effect of the air bubbles G. Within the above range, the air bubbles G roll or smoothly slide along the bubble discharge surface 17 without adhering to and staying on the bubble discharge surface 17 and thus can be discharged almost reliably from the fluid injection hole 16A and the fluid injection port 16. Further, in a case where the inclination angle α of the bubble discharge surface 17 is too large as compared with the above range, the capacity of the flow channel end part 12 becomes too large, which may cause a problem in that the amount of reagent to be consumed increases.

In this embodiment, since the thickness of the lid part 14 is substantially constant, the upper surface of the lid part 14, that is, the upper surface of the fluid storage part is also inclined in a truncated cone shape. For this reason, the surface of the fluid storage part also inclines downward as the distance from the fluid injection port 16 increases, and the fluid spilled from the fluid injection port 16 is accumulated in the peripheral part of the lid part 14 that is away from the fluid injection port 16. As a result, it is possible to reduce the risk that the spilled fluid flows inward again from the fluid injection port 16 to cause contamination. However, the present invention is not limited to this constitution, and the upper surface of the lid part 14, that is, the upper surface of the fluid storage part can be made horizontal by thickening the thickness of the lid part 14 as the distance from the fluid injection port 16 increases.

In this embodiment, the fluid injection port 16 is caused to stand up from the lid part 14. However, instead, the fluid injection hole 16A may be opened as it is without forming in the lid part 14 the fluid injection port 16 that has stood up.

The inner circumference of the upper end of the fluid injection port 16 is chamfered, in terms of the cross-sectional shape, over the entire circumference to form an annular chamfered portion 16B. The chamfered portion 16B is formed in a shape that matches well with a tip of an instrument such as a pipette, a micropipette, or a dispenser for injecting a fluid (a reagent or a dispersion liquid) from the fluid injection port 16, and thus the pointed tip of the instrument can airtightly abut with the fluid injection port 16. The shape of the fluid injection port 16 is not limited to a cylindrical shape. It may be a rectangular tubular shape or a polygonal tubular shape as necessary, and it may be an annular shape in which the periphery of the fluid injection hole 16A is slightly raised, or simply the opening portion as described above. In addition, the fluid injection port 16 may be a conical opening portion formed by denting the surface of the lid part 14.

At a lower end of the partitioned part 28 on the side of the fluid injection part 8, a step portion 34 having a constant height from the lower surface is formed over the entire length of the partitioned part 28, and above the step portion 34, each of two ribs 30 that reach the upper end of the partitioned part 28 is formed to extend in the vertical direction. The rib 30 enhances the bending strength of the partitioned part 28. In addition, in the partitioned part 28, each of an engagement groove 32 having a constant depth, opening on the lower surface of the step portion 34, and an engagement ridge 42 adjacent to the engagement groove 32 on the side of the cell placement membrane 6 is formed.

As shown in FIG. 6, the engagement groove 32 having a constant depth, opening on the lower surface of the peripheral wall portion 22, and the engagement ridge 42 adjacent to the engagement groove 32 on the side of the cell placement membrane 6 are also formed at two linearly extending places in the peripheral wall portion 22 of the outer frame body 20. The engagement groove 32 and engagement ridge 42 at the two linearly extending places are respectively connected to the engagement groove 32 and the engagement ridge 42 of the partitioned part 28, thereby forming a rectangular shape when viewed in plan view.

A rectangular tubular frame body 36 having a rectangular shape in plan view is attachably and detachably accommodated in a square space surrounded by two linearly extending places in the peripheral wall portion 22 and two partitioned parts 28. As shown in FIG. 8, the cell placement membrane 6 is stretched over the entire surface of the lower end of the frame body 36 with the wells 50 facing upward, and the lower end of the frame body 36 and the cell placement membrane 6 are all joined without any gaps over the entire circumference. The frame body 36 is made of a flexible plastic or the like, and thus it is configured such that in a case where a force to spread the frame body 36 outward is applied, four walls thereof slightly spread outward, tension is applied to the cell placement membrane 6, and slack in the cell placement membrane 6 can be prevented.

The thickness of the cell placement membrane 6 is not limited. However, it is preferably set to be about 5 to 100 μm and more preferably about 10 to 50 μm from the viewpoints of forming a well 50 which target cells enter one by one and forming a fine through-hole 52 that allows a fluid to flow from the bottom of the well 50 to the back surface side. The cell placement membrane 6 may be a multilayer membrane having two or more layers. In that case, a through-hole to be the well 50 is formed in the upper layer, a through-hole to be the through-hole 52 is formed in the lower layer, and then these two layers are bonded together to form the well 50 and the through-hole 52.

The material of the cell placement membrane 6 is not limited, and it is generally desirable that, in terms of molding accuracy and cost, the cell placement membrane 6 be made of various plastics that are harmless to the target cells; however, as necessary, it may be made of any material such as an inorganic compound such as ceramic, polycrystal or single crystal silicon, or glass, or a metal. The well 50 and the through-hole 52 can also be formed by etching or photolithography.

From the viewpoint of increasing the disposition density according to the average shape of the cells C to be captured, the planar shape of the well 50 is preferably hexagonal or circular as shown in FIG. 8; however, as necessary, it may be quadrangular such as square, or polygonal, elliptical, or the like. The size of the well 50 should be selected according to the size of the cells C to be caught, and thus it is not limited. However, in general, it is desirable that the maximum diameter of the circle that enters the well opening portion be about 1 to 100 µm and the depth thereof be about 1 to 100 µm so that one cell C enters one well 50, but two or more cells C hardly enter one well 50. A plurality of kinds of frame bodies 36 having the cell placement membranes 6, differing in the size of the well 50, may be prepared and combined with a common bottom plate part 2 and the outer frame body 20 to constitute a cell screening kit.

Regarding the size of the cells C, the maximum diameter of the circle that enters the well 50 in plan view may be about 0.5 to 2 times and is more preferably 0.8 to 1.9 times the maximum diameter of the cells C to be collected. The depth of the well 50 may be about 0.5 to 4 times and more preferably 0.8 to 1.9 times the maximum diameter of the cells C to be collected. It is preferable that the shortest distance between the well 50 and the wells 50 adjacent to each other be about 1 to 10 µm since the density of the wells 50 can be increased; however, this range is not limited to this.

Two through-holes 52 in this example are formed in the center of the bottom surface of each well 50. It is preferable that a plurality of through-holes be formed in this manner since clogging is unlikely to occur. However, the present invention is not limited to this, and in the present invention, one through-hole or three or more through-holes may be formed in the center of one well 50, or a plurality of through-holes 52 may be formed at random or at lattice point positions on the bottom surface of the well 50. The inner diameter of the through-hole 52 is not limited. However, the minimum inner diameter is preferably in a range of about 10 nm to 20 µm so that the cells C do not pass through, and it is preferably 0.5 times or less the average diameter of the cells C to be caught in the well 50.

Figure 4:
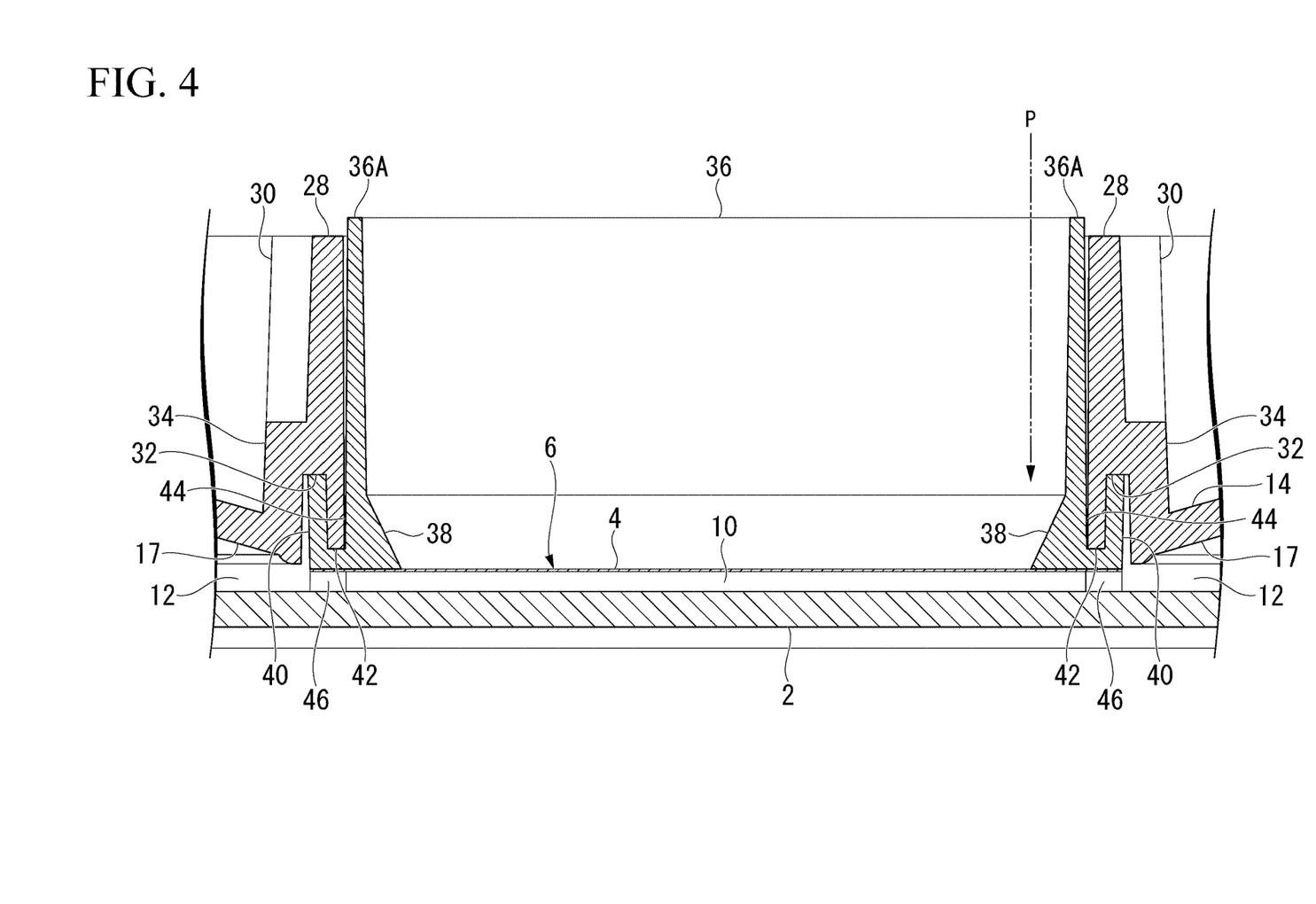
FIG. 4 is a real cross-sectional view of a central part of the cell screening device according to the same embodiment.

As shown in FIG. 4 and FIG. 6, on the outer circumference surface of the lower end part of the frame body 36, an engagement groove 44 that opens upward and an engagement ridge 40 that protrudes downward are formed over the entire circumference by making the shape thereof folded upward. The depth of the engagement groove 44 and the vertical width of the engagement ridge 40 are substantially constant over the entire circumference of the frame body 36. The engagement ridge 40 is inserted into the engagement groove 32 formed on the lower surface of the outer frame body 20, and the engagement ridge 42 of the outer frame body 20 is inserted into the engagement groove 44 of the frame body 36. By these fittings, the frame body 36 is fixed to the outer frame body 20 in a state where the frame body 36 is accommodated inside the central space of the outer frame body 20.

At this time, the lower end surface of the frame body 36 is abutted on the upper surface of the spacer 46 formed in the bottom plate part 2, and the thickness of the spacer 46 causes the separation amount of the cell placement membrane 6 from the bottom plate part 2, that is, the thickness of the flow channel 10 to be accurately defined. In this embodiment, as shown in FIG. 7, a pair of spacers 46 having a U-shape in plan view are formed inside the engagement wall 18 along the lower end shape of the frame body 36, and a notch 47 is formed between the spacers 46. In a state where the frame body 36 is fixed on the bottom plate part 2, it is configured such that a fluid flows from the flow channel 10 to each flow channel end part 12 through these notches 47. The spacer 46 may not have the shape as shown in the drawing, and it suffices that the spacer abuts with the lower surface of the frame body 36 at several places. In some cases, it may be configured so that the height of the frame body 36 from the bottom plate part 2 is accurately defined by the engagement with the outer frame body 20 without forming the spacer 46.

An inclined surface 38 having a constant width is formed on the inner circumference surface of the lower end part of the frame body 36 over the entire circumference, and the inclined surface 38 protrudes toward the cell placement membrane 6 as it goes downward. Due to the formation of such an inclined surface 38, in a case where target cells are sucked up from the well 50 of the cell placement membrane 6 with an instrument P such as a pipette, a micropipette, or a dispenser, it is possible to easily suck out the cells with the instrument P even in a case where the well 50 in which the collected cells are present is located just near the inner circumference of the frame body 36 as shown in FIG. 4. Further, the inclined surface 38 also has an effect of increasing the adhesion area of the cell placement membrane 6 to the frame body 36 and thus increasing the joining strength of the cell placement membrane 6, and it is also useful for increasing the strength of the frame body 36.

Figure 1:
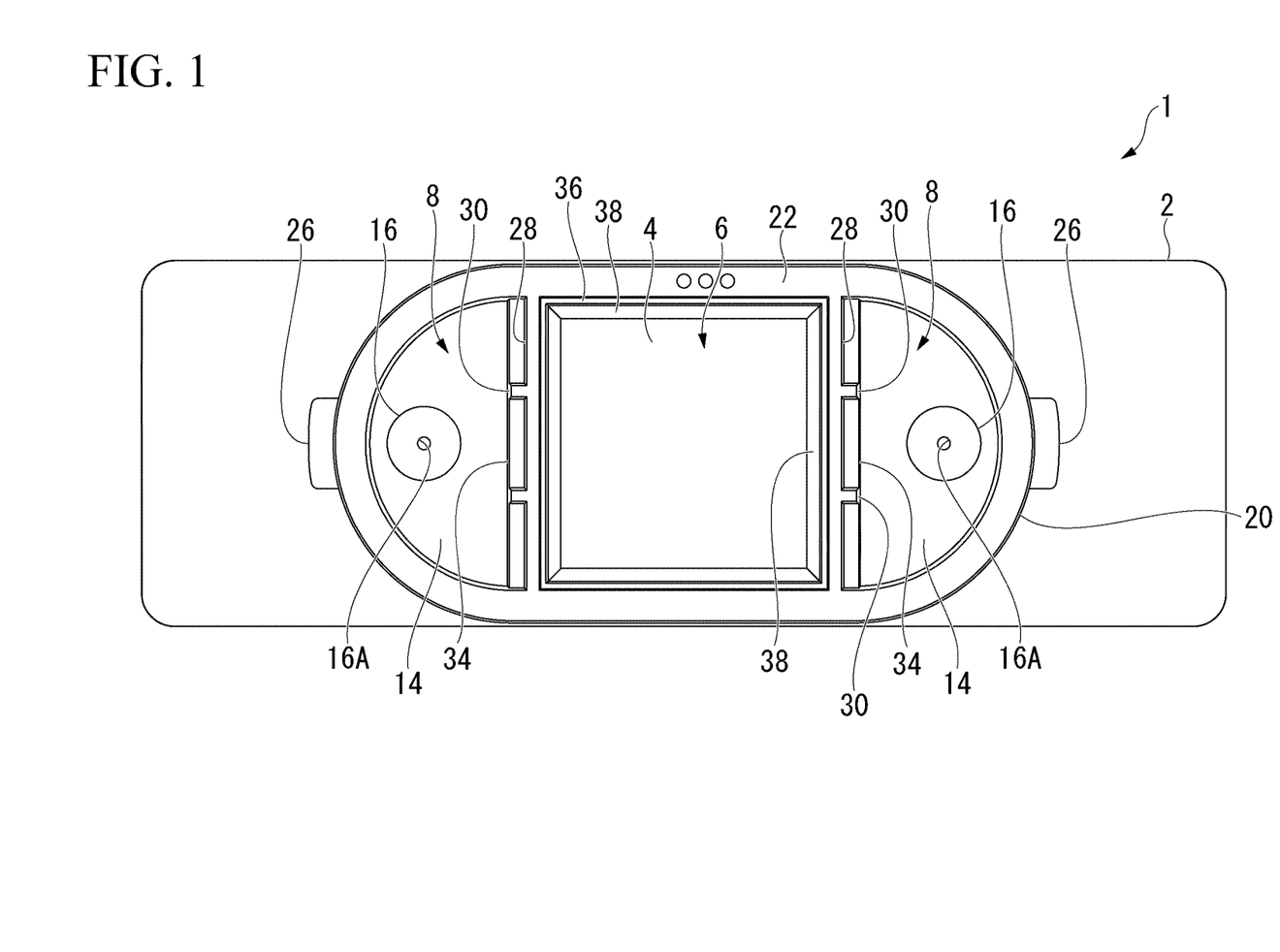
FIG. 1 is a plan view showing a cell screening device according to an embodiment of the present invention.
Figure 2:
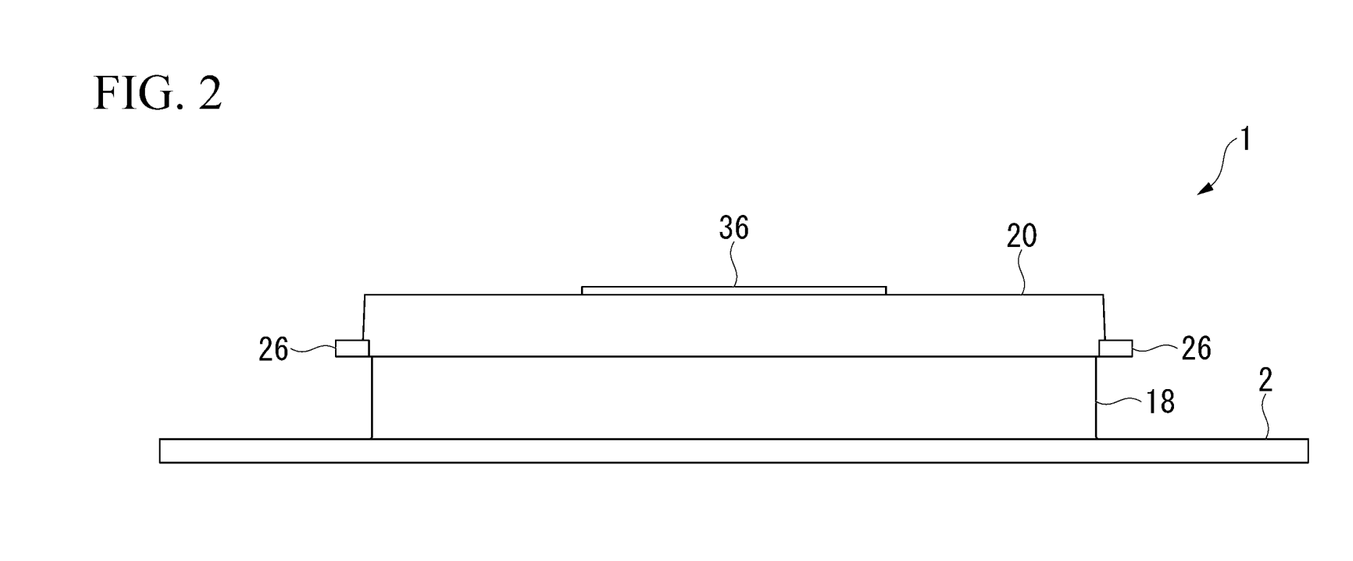
FIG. 2 is a front view of the cell screening device according to the same embodiment.

In a case of manufacturing a cell screening device having the above constitution, in a state where the bottom plate part 2, the frame body 36, and the outer frame body 20 have been individually formed as shown in FIG. 7, first, the frame body 36 is fitted into the lower surface of the outer frame body 20, and then the outer frame body 20 is fitted into the engagement wall 18 of the bottom plate part 2, whereby the completed state as shown in FIG. 1 and FIG. 6 is obtained.

In the process of fitting the frame body 36 into the lower surface of the outer frame body 20, as shown in FIG. 4 and FIG. 6, the engagement ridge 42 of the outer frame body 20 is fitted into the engagement groove 44 of the frame body 36, and the engagement ridge 40 of the frame body 36 is fitted into the engagement groove 32 of the outer frame body 20, whereby both are firmly fixed by the elasticity of each engaging part. At the same time, the inner circumference surface of the engagement ridge 40 and the outer circumference surface of the engagement ridge 42 have a shape in which at least one of them is slightly inclined upward as it goes upward. As a result, as the engagement progresses, the engagement ridges 40 on the four sides of the frame body 36 are pulled outward by the engagement ridges 42 of the outer frame body 20, the lower end part of the frame body 36 is slightly expanded in all directions, and this causes tension to pull the four sides of the cell placement membrane 6, whereby a uniform tension is applied to the cell placement membrane 6.

As a result, even in a case where there is slight slack in the cell placement membrane 6 when the frame body 36 is in the free state, slack in the cell placement membrane 6 is eliminated in a case where the frame body 36 is fixed to the outer frame body 20, and the flatness of the cell placement surface 4 on which a large number of wells 50 of the cell placement membrane 6 are formed is increased, and in a case where the cell placement surface 4 is filled with a dispersion liquid in which cells are dispersed, and then the cells are made to float evenly, for example, by shaking the cell screening device, it is possible to obtain an advantage in that it is easy to capture the cells one by one in the wells 50.

A cell screening kit using the present embodiment includes a cell screening device 1 and a bead (a detection particle) B that is a carrier particle on which a substance having a binding property to a secretion product of cells to be screened is immobilized. The cell screening kit is a product that accommodates, in an outer container such as a box, one or more cell screening devices 1 and an inner container in which a large number of fine beads B, which are detection particles, are contained in a state of powder or suspended in a dispersion liquid and encapsulated.

The kind of binding particle is not limited; however, it may be, for example, a carrier particle consisting of a bead (a magnetic bead, a resin bead, or the like), a hydrogel particle (sodium alginate gel, agarose gel, or the like), a metal particle (a gold nanoparticle), and the like, or a catcher capable of binding to an antibody that is secreted from an antibody-producing target cell, where the antibody is attached to a carrier particle. The particle size of the binding particle is not limited; however, in general, the maximum diameter of the particle is preferably about 100 nm to 50 µm and more preferably about 500 nm to 30 µm.

In a case of carrying out actual screening, cells and the beads B, which are the detection particles, are dispersed in a dispersion liquid and applied onto the cell placement membrane 6, the cell screening device 1 is shaken or the cells C are discharged to the flow channel 10 through the through-hole 52 to put the cells C one by one into the well 50, a large number of beads B are put into the well 50 together with each cell C, and the excess dispersion liquid is discharged to the flow channel 10 through the through-hole 52. In a case where the antibody in the secretion product of the cell C is reacted with the catcher of the beads B in this state, only the reacted beads B can be visualized with a fluorescently labeled antibody to find the target cell.

According to the cell screening device 1 having the above constitution, since the bubble discharge surface 17 that rises as it approaches a fluid injection hole 16A is formed on the back side of each lid part 14, that is, on the ceiling surface of the flow channel end part 12, the air bubbles G that have entered the flow channel end part 12 rise along the bubble discharge surface 17 and then become discharged from the fluid injection port 16. As a result, it is possible to suppress screening problems such that, for example, the air bubbles G enter the flow channel 10, abut on the back surface of the cell placement membrane 6, and thus the through-holes 52 and the wells 50 are blocked, and that a fluid cannot uniformly enter and exit each well 50.

Further, in this embodiment, since the bubble discharge surface 17 is formed over the entire surface of the ceiling surface of the flow channel end part 12 in the lid part 14, it is possible to obtain an advantage in that the air bubbles G move toward the fluid injection hole 16A along the bubble discharge surface 17 and become discharged from the fluid injection port 16 even in a case where the air bubbles G are located at any position in the flow channel end part 12.

However, the present invention is not limited to the constitution of the formation on the entire surface, and the formation may be carried out partially around only the fluid injection hole 16A on the ceiling surface of the flow channel end part 12, for example, in an annular shape. Also in this case, since the air bubbles G that have entered from the fluid injection hole 16A move toward the fluid outlet 16A along the air bubble discharge surface formed around the fluid injection hole 16A and then become discharged, the effect of discharging bubbles is generally obtained sufficiently. In addition, since the degree of protrusion of the lid part 14 can be reduced to be small, there is an advantage in that the degree of freedom in the design of the cell screening device is increased by partially forming the bubble discharge surface.

Further, in this embodiment, since the flow channel end parts 12 located at both ends of the flow channel 10 are blocked by lid parts 14, and the fluid injection port 16 having the fluid injection hole 16A communicating with the flow channel 10 is provided in these lid parts 14, the movement of the fluid in the flow channel end part 12 and the flow channel 10 can be suppressed by the lid part 14, and the fluid can be injected in and taken out of the flow channel 10 through the fluid injection port 16. As a result, even in a case where the cell screening device 1 is carried or inclined with the cells C being caught in the well 50 of the cell screening device 1 and a fluid such as a dispersion liquid being put into the flow channel 10, it becomes difficult for the fluid to move along the flow channel 10 and the flow channel end part 12, and it is possible to suppress a so-called sloshing phenomenon. Accordingly, it is also possible to suppress the problem in which some of the dispersion liquid flows into the well 50 through the through-hole 52 and the cells C and the beads B caught in the well 50 are released.

Further, in this embodiment, as shown in FIG. 5, even in a case where the fluid L overflows from the fluid injection hole 16A of the fluid injection port 16, the fluid storage part (the peripheral part on the upper surface of the lid part 14) receives the fluid L, whereby it is possible to suppress the reentry into the flow channel 10 from the fluid injection port 16, and it is possible to reduce, for example, the risk of contamination from the outside. Since the partitioned part 28 is formed between the cell placement surface 4 and the lid part 14, it is possible to suppress the flow of the fluid to the cell placement part 6 even in a case where the fluid is accumulated in the fluid storage part 14.

Further, in this embodiment, since the two fluid injection ports 16 are formed at both ends of the flow channel 10, it is possible to realize a wide range of usage methods, for example, causing the fluid to flow from one fluid injection port 16 into the flow channel 10 and causing the excess fluid to be discharged from the other fluid injection port 16.

Further, in this embodiment, since the cell placement membrane 6 is positioned at the correct position on the bottom plate part 2 by causing the lower end of the frame body 36 to abut with the spacer 46 of the bottom plate part 2, the flow of the fluid between the well 50 and the flow channel 10 becomes as desired, and highly accurate screening becomes possible.

Further, in this embodiment, since the bottom plate part 2 and the outer frame body 20 are formed as separate ones, and the lid part 14 and the peripheral wall portion 22 can be disposed at an accurate position with respect to the bottom plate part 2 by attaching the outer frame body 20 to the bottom plate part 2, it is easy to assemble the cell screening device 1. After use, it is also possible to remove the outer frame body 20 from the bottom plate part 2, which facilitates maintenance.

Further, in this embodiment, the cell placement membrane 6, the lid part 14, and the peripheral wall portion 22 can be accurately positioned simply by forming the bottom plate part 2, the outer frame body 20, and the frame body 36 as separate ones, and attaching the frame body 36 and the outer frame body 20 to the bottom plate part 2, and thus the ease of assembly can be improved. After use, it is also possible to remove the frame body 36 and the outer frame body 20 from the bottom plate part 2, which facilitates maintenance.

Further, in this embodiment, the cell placement part 6, the lid part 14, the peripheral wall portion 22, and two fluid injection ports 16 can be accurately positioned simply by forming the bottom plate part 2 and the outer frame body 20 as separate ones, and attaching the outer frame body 20 to the bottom plate part 2, and thus assembly is easy.

Further, in this embodiment, since the fluid injection port 16 has a cylindrical shape, it is easy to take in and take out the fluid by almost airtightly applying a conical pointed tip of a pipette, a dispenser, or the like.

According to the cell screening kit of this embodiment, in a state where the cells C are incorporated into individual wells 50, detection particles B and secretion product of the cells are reacted in the wells 50, and screening can be carried out by luminescence from the detection particles B. Moreover, in a case where a reagent or a dispersion liquid is injected in or taken out through the fluid injection port 16 using an instrument such as a pipette, a micropipette, a dispenser, or the like, or in a case where the device is inclined and thus the liquid level inside the flow channel end part 12 drops, since a bubble discharge surface 17 is formed at the back side of the lid part 14, that is, the ceiling surface of the flow channel end part 12, air bubbles move toward the fluid outlet 16A along the bubble discharge surface 17 and then become discharged from the fluid injection port 16 even in a case where air bubbles enter the flow channel end part 12. Accordingly, it is difficult for air bubbles to enter the flow channel 10, and thus the risk that, for example, screening is affected is low.

Figure 9:
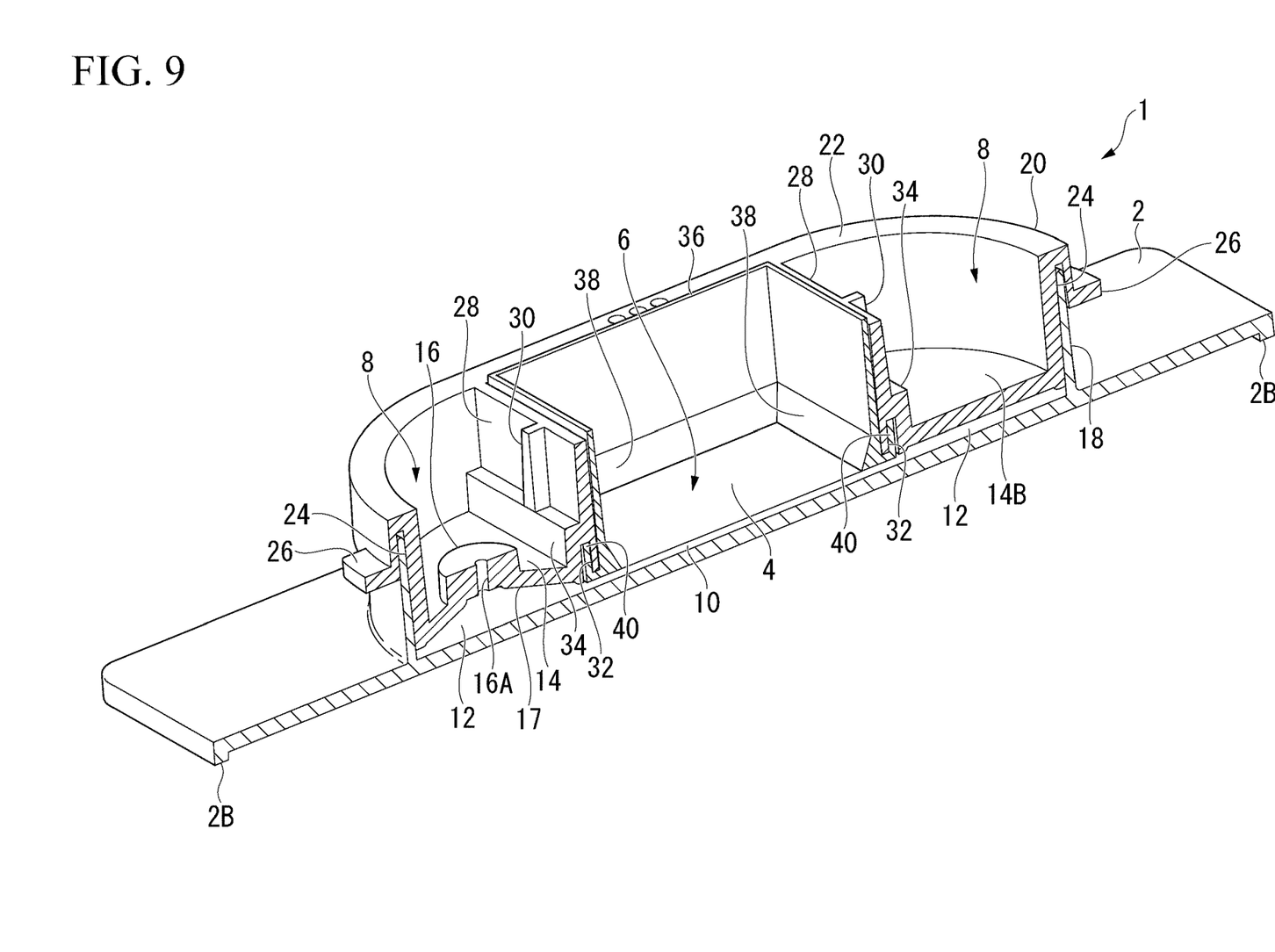
FIG. 9 is a perspective view showing a real cross section of a cell screening device according to another embodiment of the present invention.

The above embodiment has the constitution in which the bubble discharge surface 17 and the fluid injection port 16 are provided in the lid part 14 at both ends of the cell screening device 1; however, as shown in FIG. 9, a constitution in which the bubble discharge surface 17 and the fluid injection port 16 are provided in the lid part 14 at one end of the cell screening device 1 is also possible. In this case, the fluid can be injected in and taken out through only one fluid injection port 16.

Figure 10:
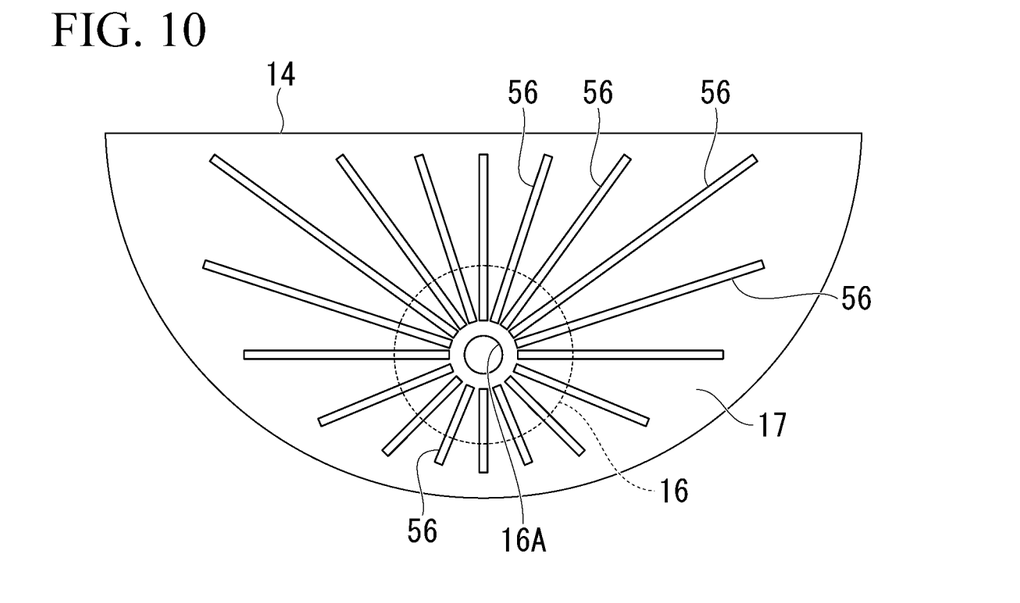
FIG. 10 is a plan view of a bubble discharge surface of the cell screening device according to the other embodiment of the present invention.

Further, in the above embodiment, the bubble discharge surface 17 has a smooth inclined surface; however, as shown in FIG. 10, a rib 56 that regulates the movement of the air bubbles G, on the back surface of the lid part 14, that is, the ceiling surface of the flow channel end part 12 may be formed. In the example of FIG. 10, ribs 56 that extend radially with the fluid injection hole 16A as a center are formed to have a length that reaches the circumferential part of the lid part 14. The cross-sectional shape of the rib 56 may be a rectangular shape or a triangular shape having a pointed tip. In a case where such ribs 56 are formed, since the movement direction of the air bubbles G is directed toward the fluid injection hole 16A by the ribs 56, the air bubbles G are smoothly discharged, and the distance between the ribs 56 is narrowed as the ribs 56 approach the fluid injection hole 16A. As a result, the air bubbles G are divided by the ribs 56 to become small air bubbles G, and the effect of facilitating discharge of them from the fluid injection hole 16A can also be obtained. The rib 56 does not have to reach the circumference of the lid part 14 and may be formed only around the fluid injection hole 16A. A groove may be formed instead of the rib 56.

Figure 11:
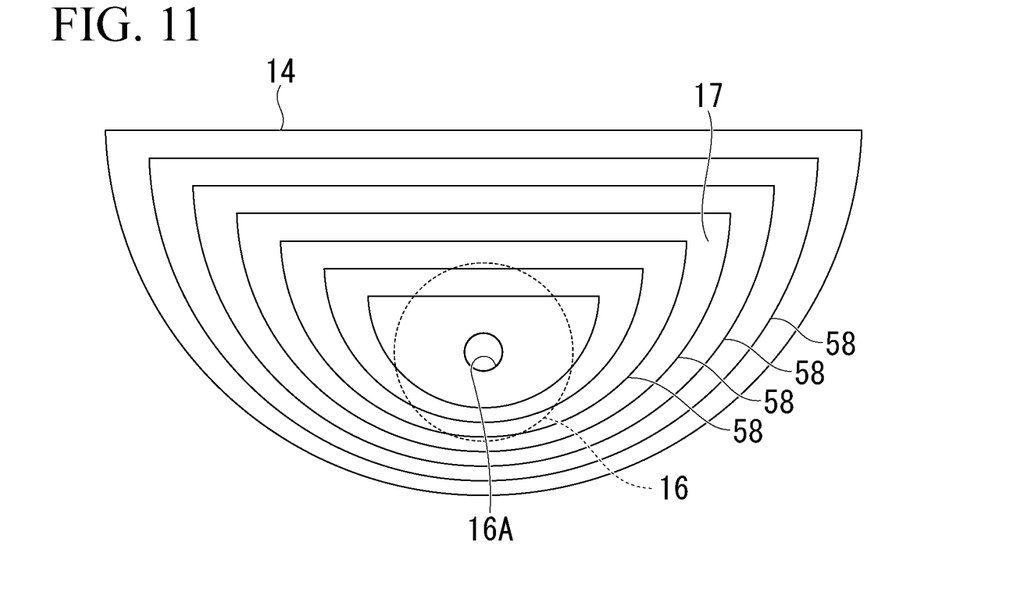
FIG. 11 is a plan view of a bubble discharge surface of the cell screening device according to the other embodiment of the present invention.

Further, as shown in FIG. 11, the bubble discharge surface 17 may be formed to have a large number of horizontal stepped surfaces 58 that gradually become high toward the fluid injection hole 16A. Also in this case, since the air bubbles G go up to the stepped surfaces 58 one after another toward the fluid injection hole 16A, they can be discharged from the fluid injection port 16. It is desirable that the width of the stepped surface 58 be sufficiently small so that the air bubbles G can go up well. In a case where such stepped surfaces 58 are formed, there is an advantage in that the air bubbles G do not easily move to the flow channel 10 side even in a case where the cell screening device 1 is inclined.

As described above, the embodiments of the present invention have been described. However, the present invention is not limited to these embodiments, and within the scope of the claims, the constitutions may be combined with each other, some constitutions may be omitted, and a known constitution may be added in each of the embodiments.

INDUSTRIAL APPLICABILITY

According to a cell screening device or a cell screening kit of the present invention, in a case where a liquid is injected in or taken out through a fluid injection hole using an instrument, or in a case where the device is inclined and thus the liquid level inside a flow channel end part drops, since a bubble discharge surface is formed on at least a part of the back side of a lid part, that is, a ceiling surface of the flow channel end part, the bubble discharge surface rising in an inclined surface shape or a stepped shape as it approaches the fluid injection hole, air bubbles move toward a fluid outlet and then become discharged from the fluid outlet along the bubble discharge surface even in a case where air bubbles enter a flow channel end part. Accordingly, it is difficult for air bubbles to enter the flow channel, and thus the effect of reducing the risk that, for example, screening is affected is exhibited. As a result, the present invention can be industrially applicable.

REFERENCE SIGNS LIST

1: Cell screening device
2: Bottom plate part
4: Cell placement surface
6: Cell placement membrane (cell placement part)
8: Fluid injection part
10: Flow channel
12: Flow channel end part
14: Lid part (fluid storage part)
16: Fluid injection port
16A: Fluid injection hole
17: Bubble discharge surface
18: Engagement wall
20: Outer frame body
22: Peripheral wall portion
24: Engagement groove
26: Protrusion
28: Partitioned part
30: Rib
32: Engagement groove 34: Step portion
36: Frame body
36A: Wall
38: Inclined surface
40: Engagement ridge
42: Engagement ridge
44: Engagement groove
46: Spacer
47: Notch
50: Well
52: Through-hole
56. Rib
58: Stepped surface
C: Cell
B: Bead
L: Dispersion liquid
G: Air bubble

The invention claimed is:

1. A cell screening device, comprising:
a bottom plate part;
a cell placement part that is provided above the bottom plate part and has a cell placement surface thereon; and
a fluid injection part that is provided on the bottom plate part, which is horizontally separated from the cell placement part;
wherein a plurality of wells are formed on the cell placement surface of the cell placement part and have a size in which cells to be screened are individually accommodatable;
a flow channel is provided between the bottom plate part and the cell placement part, the flow channel having a flow channel end part extending to the fluid injection part;
each of the wells having a through-hole that leads to the flow channel from an inner bottom surface of each of the wells, the through hole having an inner diameter through which the cells to be screened are not passable;
the fluid injection part having a lid part that is horizontally separated by a partition from the cell placement part and the lid part airtightly blocks the flow channel end part;
the partition is higher than the fluid injection part;
a fluid injection hole provided in the lid part and leads to the flow channel end part; and
a bubble discharge surface is formed on a ceiling surface of the flow channel end part, which is a lower surface of the lid part, to surround the fluid injection hole, and the bubble discharge surface rises in an inclined surface shape or a stepped shape as the bubble discharge surface approaches the fluid injection hole.

2. The cell screening device according to claim 1, wherein the bubble discharge surface is formed over an entire surface of the ceiling surface of the flow channel end part in the lid part.

3. The cell screening device according to claim 1, wherein the bubble discharge surface is an inclined surface having a linear cross-sectional or curved cross-sectional shape, which is inclined by 5° to 45° with respect to a lower surface of the bottom plate part.

4. The cell screening device according to claim 1,
wherein the bottom plate part has a rectangular shape having a long side and a short side, the fluid injection part, the lid part, the fluid injection hole, and the bubble discharge surface are each formed on both sides of the bottom plate part in a longitudinal direction.

5. The cell screening device according to claim 1,
wherein the cell placement part is a membrane body,
a plurality of the wells are formed on an upper surface of the membrane body in a lattice form, and the through-hole that leads to the inner bottom surface of each of the wells is formed on a lower surface of the membrane body,
a frame body supports a periphery of the membrane body and surrounds the cell placement surface, and
an engaging part for detachably fixing the frame body is provided in the bottom plate part.

6. The cell screening device according to claim 5,
wherein a standing peripheral wall portion is formed in a circumference of the lid part,
the lid part and the peripheral wall portion are formed as an outer frame body that is detachably fixed on the bottom plate part, and
the frame body that supports the membrane body is detachably fixed to the outer frame body.

7. The cell screening device according to claim 1,
wherein a peripheral wall portion that stands up from a circumference of the lid part is formed, and
the lid part and the peripheral wall portion are formed as an outer frame body that is detachably fixed on the bottom plate part.

8. The cell screening device according to claim 1, wherein a tubular port that stands up from a periphery of the fluid injection hole is formed on an upper surface of the lid part.

9. The cell screening device according to claim 1, wherein the fluid injection hole has a circular shape.

10. The cell screening device according to claim 1, wherein the fluid injection hole has a circular shape, and
a circular port is formed on an upper surface of the lid part to stand up from a periphery of the fluid injection hole.

11. The cell screening device according to claim 1, wherein the bubble discharge surface has a truncated cone shape with the fluid injection hole as an apex.

12. The cell screening device according to claim 11, wherein an upper surface of the lid part is formed in a truncated cone shape so that fluid spilled from the fluid injection port can be accumulated in a peripheral area of the upper surface of the lid part that is away from the fluid injection port.

13. A cell screening kit, comprising:
the cell screening device according to claim 1; and
a detection particle that is a carrier particle on which a substance having a binding property to a secretion product of cells to be screened is immobilized.

* * * * *